US006271361B1

(12) United States Patent
Alnemri et al.

(10) Patent No.: US 6,271,361 B1
(45) Date of Patent: Aug. 7, 2001

(54) APOPTOTIC PROTEASE MCH6, NUCLEIC ACIDS ENCODING SAME AND METHODS OF USE

(75) Inventors: Emad S. Alnemri; Teresa Fernandes-Alnemri, both of Ambler; Gerald Litwack, Wynnewood, all of PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/257,218

(22) Filed: Feb. 25, 1999

Related U.S. Application Data

(62) Division of application No. 08/865,579, filed on May 29, 1997.

(51) Int. Cl.[7] .................................................. C12N 15/57
(52) U.S. Cl. .................... 536/23.2; 536/23.5; 435/320.1; 435/69.1; 435/226
(58) Field of Search ................................. 536/23.2, 23.5, 536/23.1; 435/226, 320.1, 69.1

(56) References Cited

U.S. PATENT DOCUMENTS 6,010,878 * 1/2000 Dixit et al. .......................... 435/69.1

OTHER PUBLICATIONS

The Merck Index, Eight Edition. 1968 Stecher et al, eds. Rahway: Merck & Co. p. 511.*
Duan et al. ICE–LAP6, a novel member of the ICE/Ced–3 gene family is activated by the cytotoxic T cell protease Granzyme B. J. Biological Chemistry 271(28): 16720–16724, 1996.*
Callard et al. the Cytokine FactsBook. San Diego: Academic Press. p. 31, 1994.*
P. Henkart, "Ice family protease: Mediators of all apoptotic cell death?" Immunity 4: 195–201, 1996.*
Alnemri et al., "Cloning and Expression of Four Novel Isoforms of Human Interleukin–1β Coverting Enzyme with Different Apoptotic Activities," *J. Biol. Chem. 270*: 4312–4317, 1995.
Alnemri et al., "Human ICE/CED–3 Protease Nomenclature," *Cell 87*: 171, 1996.
Black et al., "Activation of Interleukin–1β by a Co–induced Protease," *FEBS Lett. 247*: 386–390, 1989.
Cerretti et al., "Molecular Cloning of the Interleukin–1β Converting Enzyme," *Science 256*: 97–100, 1992.
Duan et al., "ICE–LAP6, a Novel Member of the ICE/Ced–3 Gene Family, is Activated by the Cytotoxic T Cell Protease Granzyme B," *J. Biol. Chem. 271*: 16720–16724, 1996.
Enari et al., "Involvement of an ICE–like Protease in Fas–Mediated Apoptosis," *Nature 375*: 78–81, 1995.

Faucheu et al., "A Novel Human Protease Similar to the Interleukin–1β Converting Enzyme Induces Apoptosis in Transfected Cells," *EMBO 14*: 1914–1922, 1995.
Fernandes–Alnemri et al., "CPP32, a Novel Human Apoptotic Protein with Homology to *Caenorhabditis elegans* Cell Death Protein Ced–3 and Mammalian Interleukin–1β–Converting Enzyme," *J. Biol. Chem. 269*: 30761–30764, 1994.
Fernandes–Alnemri et al., "In Vitro Activation of CPP32 and Mch3 by Mch4, a Novel Human Apoptotic Cysteine Protease Containing two FADD–like domains," *Proc. Natl. Acad. Sci. USA 93*: 7464–7469, 1996.
Fernandes–Alnemri et al., "Mch2, a New Member of the Apoptotic Ced–3–Ice Cysteine Protease Gene Family," *Cancer Res. 55*: 2737–2742, 1995.
Fernandes–Alnemri et al., "Mch3, a Novel Human Apoptotic Cysteine Protease Highly Related to CPP32," *Cancer Res. 55*: 6045–6052, 1995.
Gagliardini et al., "Prevention of Vertebrate Neuronal Death by the crmA Gene," *Science 263*: 826–828, 1994.
Golstein, "Controlling Cell Death," *Science 275*: 1081–1082, 1997.
Kamens et al., "Identification and Characterization of ICH–2, a Novel Member of the Interleukin–1β–Converting Enzyme Family of Cysteine Proteases," *J. Biol. Chem. 270*: 15250–15256, 1995.
Kim, Junga, Public Release Date of Genbank Accession No. U56390, GenBank Submission Staff, 1997.
Kumar et al., "Induction of Apoptosis of the Mouse Nedd2 Gene, Which Encodes a Protein Similar to the Product of the *Caenorhabditis elegans* Cell Death Gene ced–3 and the Mammalian IL–1β–Converting Enzyme," *Genes Dev. 8*: 1613–1626, 1994.
Martin et al., "Cell–Free Reconstitution of Fas–, UV Radiation– and Ceramide–Induced Apoptosis," *EMBO 14*: 5191–5200, 1995.
Miura et al., "Induction of Apoptosis in Fibroblasts by IL–1β–Converting Enzyme, a Mammalian Homolog of the C. Elegans Cell Death Gene ced–3," *Cell 75*: 653–660, 1993.

(List continued on next page.)

Primary Examiner—Christopher S. F. Low
Assistant Examiner—Gabriele E. Bugaisky
(74) Attorney, Agent, or Firm—Seed Intellectual Property Law Group PLLC

(57) ABSTRACT

The invention provides an isolated gene encoding Mch6 as well as functional fragments thereof. Also provided are isolated nucleic acid sequences encoding Mch6 or functional fragments thereof. The gene or nucleic acid sequences can be single or double stranded nucleic acids corresponding to coding or non-coding strands of the Mch6 nucleotide sequences. The invention further provides an isolated Mch6 polypeptide and isolated large and small subunits of the Mch6 polypeptide, including functional fragments thereof.

2 Claims, 5 Drawing Sheets

OTHER PUBLICATIONS

Munday et al., "Molecular Cloning and Pro–Apoptotic Activity of $ICE_{rel}II$ and $ICE_{rel}III$, Members of the ICE/CED–3 Family of Cysteine Proteases," *J. Biol. Chem.* 270: 15870–15876, 1995.

Nicholson et al., "Identification and Inhibition of the ICE/CED–3 Protease Necessary for Mammalian Apoptosis," *Nature* 376: 37–43, 1995.

Ray et al., "Viral Inhibition of Inflammation: Cowpox Virus Encodes an Inhibitor of the Interleukin–1β Converting Enzyme," *Cell* 69: 597–604, 1992.

Thompson, "Apoptosis in the Pathogenesis and Treatment of Disease," *Science* 267: 1456–1462, 1995.

Wang et al., "Ich–1, and Ice/ced–3–Related Gene, Encodes Both Positive and Negative Regulators of Programmed Cell Death," *Cell* 78: 739–750, 1994.

Walker et al., "Cyrstal Structure of the Cysteine Protease Interleukin–1β–Converting Enzyme: A $(p20/p10)_2$ Homodimer," *Cell* 78: 343–352, 1994.

Yuan et al., "The C. Elegans Cell Death Gene ced–3 Encodes a Protein Similar to Mammalian Interleukin–1β–Converting Enzyme," *Cell* 75: 641–652, 1993.

\* cited by examiner

```
ATG GAC GAA GCG GAT CGG CGG CTC CTG CGG CGG TGC CGG CTG CGG CTG   48
Met Asp Glu Ala Asp Arg Arg Leu Leu Arg Arg Cys Arg Leu Arg Leu
 1               5                  10                  15

GTG GAA GAG CTG CAG GTG GAC CAG CTC TGG GAC GCC CTG CTG AGC AGC   96
Val Glu Glu Leu Gln Val Asp Gln Leu Trp Asp Ala Leu Leu Ser Ser
             20                  25                  30

GAG CTG TTC AGG CCC CAT ATG ATC GAG GAC ATC CAG CGG GCA GGC TCT  144
Glu Leu Phe Arg Pro His Met Ile Glu Asp Ile Gln Arg Ala Gly Ser
         35                  40                  45

GGA TCT CGG CGG GAT CAG GCC AGG CAG CTG ATC ATA GAT CTG GAG ACT  192
Gly Ser Arg Arg Asp Gln Ala Arg Gln Leu Ile Ile Asp Leu Glu Thr
     50                  55                  60

CGA GGG AGT CAG GCT CTT CCT TTG TTC ATC TCC TGC TTA GAG GAC ACA  240
Arg Gly Ser Gln Ala Leu Pro Leu Phe Ile Ser Cys Leu Glu Asp Thr
 65                  70                  75                  80

GGC CAG GAC ATG CTG GCT TCG TTT CTG CGA ACT AAC AGG CAA GCA GCA  288
Gly Gln Asp Met Leu Ala Ser Phe Leu Arg Thr Asn Arg Gln Ala Ala
                 85                  90                  95

AAG TTG TCG AAG CCA ACC CTA GAA AAC CTT ACC CCA GTG GTG CTC AGA  336
Lys Leu Ser Lys Pro Thr Leu Glu Asn Leu Thr Pro Val Val Leu Arg
                100                 105                 110

CCA GAG ATT CGC AAA CCA GAG GTT CTC AGA CCG GAA ACA CCC AGA CCA  384
Pro Glu Ile Arg Lys Pro Glu Val Leu Arg Pro Glu Thr Pro Arg Pro
             115                 120                 125

GTG GAC ATT GGT TCT GGA GGA TTT GGT GAT GTC GGT GCT CTT GAG AGT  432
Val Asp Ile Gly Ser Gly Gly Phe Gly Asp Val Gly Ala Leu Glu Ser
         130                 135                 140
```

Fig. 1A

```
TTG AGG GGA AAT GCA GAT TTG GCT TAC ATC CTG AGC ATG GAG CCC TGT 480
Leu Arg Gly Asn Ala Asp Leu Ala Tyr Ile Leu Ser Met Glu Pro Cys
145                 150                 155                 160

GGC CAC TGC CTC ATT ATC AAC AAT GTG AAC TTC TGC CGT GAG TCC GGG 528
Gly His Cys Leu Ile Ile Asn Asn Val Asn Phe Cys Arg Glu Ser Gly
                165                 170                 175

CTC CGC ACC CGC ACT GGC TCC AAC ATC GAC TGT GAG AAG TTG CGG CGT 576
Leu Arg Thr Arg Thr Gly Ser Asn Ile Asp Cys Glu Lys Leu Arg Arg
                180                 185                 190

CGC TTC TCC TCG CCG CAT TTC ATG GTG GAG GTG AAG GGC GAC CTG ACT 624
Arg Phe Ser Ser Pro His Phe Met Val Glu Val Lys Gly Asp Leu Thr
                195                 200                 205

GCC AAG AAA ATG GTG CTG GCT TTG CTG GAG CTG GCG CAG CAG GAC CAC 672
Ala Lys Lys Met Val Leu Ala Leu Leu Glu Leu Ala Gln Gln Asp His
210                 215                 220

GGT GCT CTG GAC TGC TGC GTG GTG GTC ATT CTC TCT CAC GGC TGT CAG 720
Gly Ala Leu Asp Cys Cys Val Val Val Ile Leu Ser His Gly Cys Gln
225                 230                 235                 240

GCC AGC CAC CTG CAG TTC CCA GGG GCT GTC TAC GGC ACA GAT GGA TGC 768
Ala Ser His Leu Gln Phe Pro Gly Ala Val Tyr Gly Thr Asp Gly Cys
                245                 250                 255

CCT GTG TCG GTC GAG AAG ATT GTG AAC ATC TTC AAT GGG ACC AGC TGC 816
Pro Val Ser Val Glu Lys Ile Val Asn Ile Phe Asn Gly Thr Ser Cys
                260                 265                 270

CCC AGC CTG GGA GGA AAG CCC AAG CTC TTT TTC ATC CAG GCC TGT GGT 864
Pro Ser Leu Gly Gly Lys Pro Lys Leu Phe Phe Ile Gln Ala Cys Gly
                275                 280                 285
```

*Fig. 1B*

```
GGG GAG CAG AAA GAC CAT GGG TTT GAG GTG GCC TCC ACT TCC CCT GAA  912
Gly Glu Gln Lys Asp His Gly Phe Glu Val Ala Ser Thr Ser Pro Glu
    290             295                 300

GAC GAG TCC CCT GGC AGT AAC CCC GAG CCA GAT GCC ACC CCG TTC CAG  960
Asp Glu Ser Pro Gly Ser Asn Pro Glu Pro Asp Ala Thr Pro Phe Gln
305             310             315?                320

GAA GGT TTG AGG ACC TTC GAC CAG CTG GAC GCC ATA TCT AGT TTG CCC 1008
Glu Gly Leu Arg Thr Phe Asp Gln Leu Asp Ala Ile Ser Ser Leu Pro
                325             330?                335

ACA CCC AGT GAC ATC TTT GTG TCC TAC TCT ACT TTC CCA GGT TTT GTT 1056
Thr Pro Ser Asp Ile Phe Val Ser Tyr Ser Thr Phe Pro Gly Phe Val
                340             345             350

TCC TGG AGG GAC CCC AAG AGT GGC TCC TGG TAC GTT GAG ACC CTG GAC 1104
Ser Trp Arg Asp Pro Lys Ser Gly Ser Trp Tyr Val Glu Thr Leu Asp
            355             360             365

GAC ATC TTT GAG CAG TGG GCT CAC TCT GAA GAC CTG CAG TCC CTC CTG 1152
Asp Ile Phe Glu Gln Trp Ala His Ser Glu Asp Leu Gln Ser Leu Leu
        370             375             380

CTT AGG GTC GCT AAT GCT GTT TCG GTG AAA GGG ATT TAT AAA CAG ATG 1200
Leu Arg Val Ala Asn Ala Val Ser Val Lys Gly Ile Tyr Lys Gln Met
385             390             395                 400

CCT GGT TGC TTT AAT TTC CTC CGG AAA AAA CTT TTC TTT AAA ACA TCA 1248
Pro Gly Cys Phe Asn Phe Leu Arg Lys Lys Leu Phe Phe Lys Thr Ser
            405             410                 415

TAA 1251
```

*Fig. 1C*

|   |           | Large Subunit |   |   | Small Subunit |
|---|-----------|---------------|---|---|---------------|
|   |           |               | * |   |               |
| I | Mch6      | RTRTGS..LSHGCQ..FIQACGGEQ..PEPDA..DQLDA..GFVSWRDPKSGSWYV |
|   | Mch5      | RDRNGT..LSHGDK..FIQACQGDN..VETDS........NCVSYRNPAEGTWYI |
|   | Mch4      | KDRQGT..LTHGRF..FIQACQGEE..IEADA........GYVSFRHVEEGSWYI |
|   | Mch3      | GVRNGT..LSHGKE..FIQACRGTE..IQADS........GYYSWRSPGRGSWFV |
|   | Mch2      | PERRGT..LSHGEG..IIQACTGNQ..DVVDN..TEVDA..GYYSHRETVNGSWYI |
|   | CPP32     | TSRSGT..LSHGKE..IIQACRGTE..IETDS........GYYSWRNSKDGSWFI |
|   | CED-3     | PTRNGT..LSHGEE..FVQACRGER..DSVDG........QYVSWRNSARGSWFI |
| II | ICE      | PRRTGA..MSHGIR..IIQACRGDS..WFKDS..FEDDA..DNVSWRHPTMGSVFI |
|   | TX        | PPRNGA..MSHGIL..IVQACRGAN..WVKDS..LEEDA..HNVSWRDSTMGSIFI |
|   | ICErelIII | PARNGA..MSHGIL..IVQACRGEK..WVRDS..LEADS..HNVSWRDRTRGSIFI |
| III | ICH-1   | EFRSGG..LSHGVE..FIQACRGDE..DQQDG..EESDA..GTAAMRNTKRGSWYI |
|   |           | b  acc        | bac | DX  DX   | aaabaa  a  ba |

Fig. 2

APOPTOTIC PROTEASE MCH6, NUCLEIC ACIDS ENCODING SAME AND METHODS OF USE

CROSS-REFERENCE TO RELATED APPLICATION

This application is a Divisional of pending U.S. patent application Ser. No. 08/865,579, filed May 29, 1997, now pending.

This invention was made with government support under research grant AI 35035 awarded by the National Institutes of Health. The government has certain rights in the invention.

BACKGROUND OF THE INVENTION

The present invention relates generally to apoptosis, or programmed cell death, and more particularly, to a novel aspartate-specific cysteine protease that can be used to modulate apoptosis for the therapeutic treatment of human diseases.

Apoptosis is a normal physiological process of cell death that plays a critical role in regulating tissue homeostasis by ensuring that the rate of new cell accumulation produced by cell division is offset by a commensurate rate of cell loss due to cell death. It has now become clear that disturbances in apoptosis, also referred to as physiological cell death or programmed cell death, which prevent or delay normal cell turnover, can be just as important to the pathogenesis of diseases as known abnormalities in the regulation of proliferation and the cell cycle. Like cell division, which is controlled through complex interactions between cell cycle regulatory proteins, apoptosis is similarly regulated under normal circumstances by the interaction of gene products that either induce or inhibit cell death.

The stimuli that regulate the function of these apoptotic gene products include both extracellular and intracellular signals. Either the presence or the removal of a particular stimulus can be sufficient to evoke a positive or negative apoptotic signal. For example, physiological stimuli that prevent or inhibit apoptosis include, for example, growth factors, extracellular matrix, CD40 ligand, viral gene products, neutral amino acids, zinc, estrogen and androgens. In contrast, stimuli that promote apoptosis include growth factors such as tumor necrosis factor (TNF), Fas, and transforming growth factor β (TGFβ). Other stimuli that promote apoptosis include, for example, neurotransmitters, growth factor withdrawal, loss of extracellular matrix attachment, intracellular calcium and glucocorticoids. Other stimuli, including those of environmental and pathogenetic origins, can either induce or inhibit programmed cell death. Although apoptosis is mediated by diverse signals and complex interactions of cellular gene products, the results of these interactions ultimately feed into a cell death pathway that is evolutionarily conserved between humans and invertebrates.

Several gene products that modulate the apoptotic process have now been identified. Although these products can be generally separated into two basic categories, gene products from each category can function to either inhibit or induce programmed cell death. One family of gene products is related to the protein Bcl-2, which inhibits apoptosis when overexpressed in cells. Other members of this gene family include, for example, Bax, Bak, Bcl-$x_L$, Bcl-$x_S$, and Bad. While some of these proteins can prevent apoptosis, others augment apoptosis, for example, Bcl-$x_S$ and Bak, respectively.

A second family of gene products, the aspartate-specific cysteine proteases (ASCPs), are genetically related to the ced-3 gene product, which was initially shown to be required for programmed cell death in the roundworm, C. elegans. The ASCP family of proteases includes human ICE (interleukin-1-β converting enzyme), ICH-$1_L$, ICH-$1_S$, CPP32, Mch2, Mch3, Mch4, Mch5, ICH-2 and ICE$_{rel}$-III. Among the common features of these gene products are that 1) they are cysteine proteases with specificity for substrate cleavage at Asp-x bonds, 2) they share a relatively conserved pentapeptide sequence, QACRG (SEQ ID NO:79) or QACQG (SEQ ID NO:80), within the active site and 3) they are synthesized as proenzymes that require proteolytic cleavage at specific aspartate residues for activation of protease activity. In the case of ICE, cleavage of the proenzyme produces two polypeptide protease subunits of approximately 20 kDa, known as p20, and 10 kDa, known as p10, that combine non-covalently to form a tetramer comprising two p20:p10 heterodimers. Although these proteases induce cell death when expressed in cells, several alternative structural forms, such as ICEδ, ICEε, ICH-$1_S$ and Mch2β, actually function to inhibit apoptosis.

In addition to the Bcl-2 and ASCP gene families that play a role in apoptosis in mammalian cells, it has become increasingly apparent that other gene products that are important in mammalian cell death have yet to be identified. For example, in addition to Ced-3, another C. elegans gene known as Ced-4 is also required for programmed cell death in C. elegans. However, mammalian homologs of Ced-4 remain elusive and have not yet been identified. Further, it is ambiguous whether other genes belong to either of the above two apoptotic gene families or what role they may play in the programmed cell death pathway. Finally, it is unclear what physiological control mechanisms regulate programmed cell death or how the cell death pathways interact with other physiological processes within the organism. For example, it has recently been suggested that cytotoxic T-lymphocytes mediate their destructive function by inducing apoptosis in their target cells.

Apoptosis maintains tissue homeostasis in a range of physiological processes such as embryonic development, immune cell regulation and normal cellular turnover. Therefore, the dysfunction or loss of regulated apoptosis can lead to a variety of pathological disease states. For example, the loss of apoptosis can lead to the pathological accumulation of self-reactive lymphocytes such as that occurring with many autoimmune diseases. Inappropriate loss of apoptosis can also lead to the accumulation of virally infected cells and of hyperproliferative cells such as neoplastic or tumor cells. Similarly, the inappropriate activation of apoptosis can also contribute to a variety of pathological disease states including, for example, acquired immunodeficiency syndrome (AIDS), neurodegenerative diseases and ischemic injury. Treatments that are specifically designed to modulate the apoptotic pathways in these and other pathological conditions can change the natural progression of many of these diseases.

Thus, there exists a need to identify new apoptotic genes and their gene products to modulate apoptosis for the therapeutic treatment of human diseases. The present invention satisfies this need and provides related advantages as well.

SUMMARY OF THE INVENTION

The invention provides an isolated gene encoding Mch6 as well as functional fragments thereof. Also provided are isolated nucleic acid sequences encoding Mch6 or functional fragments thereof. The gene or nucleic acid sequences can be single or double stranded nucleic acids corresponding to coding or non-coding strands of the Mch6 nucleotide sequences. The invention further provides an isolated Mch6 polypeptide and isolated large and small subunits of the Mch6 polypeptide, including functional fragments thereof.

BRIEF DESCRIPTION OF THE DRAWINGS

FIGS. 1a, 1b and 1c show the nucleotide and predicted amino acid sequence of Mch6, listed as SEQ ID NO:1 and SEQ ID NO:2, respectively. The active site pentapeptide sequence QACGG (SEQ ID NO:78) is underlined. Cleavage sites after Asp315 and Asp330 are indicated by vertical arrows.

FIG. 2 shows a multiple amino acid sequence alignment of relatively conserved regions within the ASCPs. The ASCPs are Mch6 (SEQ ID NO:6, consisting of noncontiguous SEQ ID NOs:17–22), Mch5 (SEQ ID NO:7, consisting of noncontiguous SEQ ID NOs:23–27), Mch4 (SEQ ID NO:8, consisting of noncontiguous SEQ ID NOs:28–32), Mch3 (SEQ ID NO:9, consisting of noncontiguous SEQ ID NOs:33–37), Mch2 (SEQ ID NO:10, consisting of noncontiguous SEQ ID NOs:38–43), CPP32 (SEQ ID NO:11, consisting of noncontiguous SEQ ID NOs:44–48), CED-3 (SEQ ID NO:12, consisting of noncontiguous SEQ ID NOs:49–53), ICE (SEQ ID NO:13, consisting of noncontiguous SEQ ID NOs:54–59), TX (SEQ ID NO:14, consisting of noncontiguous SEQ ID NOs:60–65), ICErelIII (SEQ ID NO:15, consisting of noncontiguous SEQ ID NOs:66–71) and ICH-1 (SEQ ID NO:16, consisting of noncontiguous SEQ ID NOs:72–77).

Figure 3:
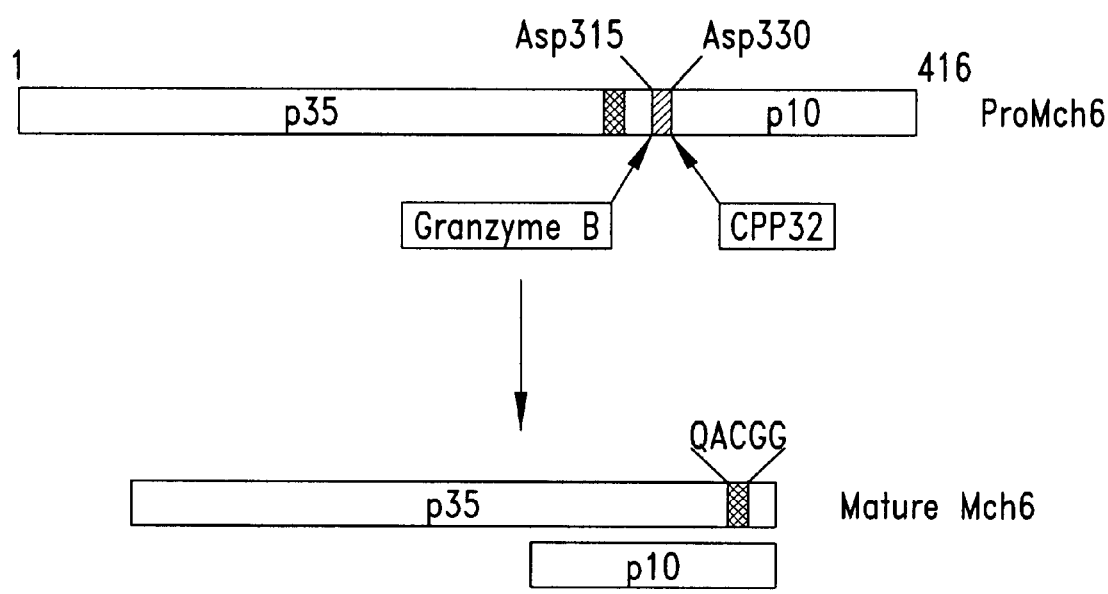

Based on the crystal structure of ICE, specific residues are indicated by lowercase letters below the sequences: "c" for residues involved in catalysis, "b" for residues that bind the substrate-carboxylate of P1 Asp and "a" for residues adjacent to the substrate P2–P4 amino acids. "DX" indicates known and potential processing sites between the small and large subunits of ASCPs. The roman numerals on the left indicate the three ASCP-subfamilies: the Ced-like subfamily (I), the ICE-like subfamily (II) and the Nedd2/Ich-1 subfamily (III). The asterisk indicates the nonconservative substitution in the active site pentapeptide sequences of Mch4, Mch5 and Mch6.

FIG. 3 shows a schematic diagram illustrating the processing of proMch6. proMch6 can be processed by CPP32 after Asp330. proMch6 can also be processed preferentially after Asp135 by granzyme B to generate the large subunit, known as p35, and the small subunit, known as p10, of mature Mch6. The active site pentapeptide QACGG (SEQ ID NO:78) in the large subunit is indicated.

DETAILED DESCRIPTION OF THE INVENTION

This invention is directed to a novel apoptotic protease termed Mch6 (mammalian ced-3 homolog 6). Mch6 is a member of the aspartate-specific cysteine protease (ASCP) family of proteases that includes, for example, ICE (Alnemri et al., *J. Biol. Chem.* 270:4312–4317 (1995)), CPP32 (Fernandes-Alnemri et al., *J. Biol. Chem.* 269:30761–30764 (1994)), Nedd2/Ich-1 (Kumar et al., *Genes & Development* 8:1613–1626 (1994); Wang et al., *Cell* 78:739–750 (1994)), Mch2 (Fernandes-Alnemri et al., *Cancer Res.* 55:2737–2742 (1995)), Mch3 (Fernandes-Alnemri et al., *Cancer Res.* 55:6045–6052 (1995), Mch4 (Fernandes-Alnemri et al., *Proc. Natl. Acad. Sci. USA* 93:7464–7470 (1996)), Mch5 (Fernandes-Alnemri et al. (1996) supra), TX (ICH-2, ICErel-II) (Faucheu et al., *EMBO* 14:1914–1922 (1995); Kamens et al., *J. Biol. Chem.* 270:15250–15256 (1995); Munday et al., *J. Biol. Chem.* 270:15870–15876 (1995)) and ICErel-III (Munday et al. (1995) supra).

Mch6 shares amino acid sequence homology with several ASCPs, but its catalytic site QACGG (SEQ ID NO:78) differs in the fourth residue from the relatively conserved catalytic sites in other known ACSPs (FIGS. 1 and 2).

Like many ASCPs, Mch6 is synthesized as a proenzyme, which can be proteolytically cleaved by, for example, CPP32 or granzyme B. The cleavage of Mch6 by these two enzymes is described further below in Examples III and IV, respectively. Cleavage of Mch6 yields two subunits, a large subunit of approximately 35 kDa and a small subunit of approximately 10 kDa, which associate to form an active heterodimer complex. Like other ASCPs, the active Mch6 complex can act as a protease and requires an Asp residue in the P1 position of the substrate binding site with a small, preferably hydrophobic, residue in the P1' position.

In one embodiment, the invention is directed to nucleic acids encoding the apoptotic protease Mch6. The nucleic acids are used to produce the recombinant Mch6 ASCP protease. The recombinant polypeptides can be used to screen for Mch6 inhibitors. Mch6 inhibitors include those that inhibit protease activity as well as compounds that inhibit Mch6 binding to other polypeptides. Such compounds are useful as pharmaceuticals for treating or preventing diseases characterized by apoptotic cell death. Alternatively, the Mch6 polypeptides can be used to screen for compounds that activate or act as agonists of Mch6, such as by inducing cleavage of the proenzyme into its active subunits. Such compounds are similarly useful as pharmaceuticals for treating or preventing diseases characterized by the loss of apoptotic cell death.

As used herein, the term "substantially" when referring to a Mch6 nucleotide or amino acid sequence is intended to refer to the degree to which two sequences of between about 15–30 or more nucleotides in length are identical or similar, so as to be considered by those skilled in the art to be functionally equivalent. For example, the Mch6 nucleic acid of the invention has a nucleotide sequence substantially the same as that shown in FIG. 1 and as SEQ ID NO:1. Thus, if a second sequence is considered by those skilled in the art to be functionally equivalent to the sequence shown as SEQ ID NO:1, then the second sequence is substantially the same as that shown as SEQ ID NO:1. Methods for sequence comparisons and determinations of similarity are well known and routine within the art.

Functionally equivalent nucleic acid sequences include, for example, sequences that are related, but different and encode the same Mch6 polypeptide due to the degeneracy of the genetic code as well as sequences that are related, but different and encode a different Mch6 polypeptide that exhibits similar functional activity. In both cases, the nucleic acids encode functionally equivalent gene products. Functional fragments of Mch6 encoding nucleic acids such as oligonucleotides, polynucleotides, primers and the like are also considered to be within the definition of the term and the invention as claimed. Functional equivalency is also relevant to Mch6 nucleic acids that do not encode gene products, for example, but instead are functional elements in and of themselves. Specific examples of such functional nucleic acids include, for example, promoters, enhancers and other gene expression and transcription regulatory elements.

An Mch6 polypeptide of the invention has an amino acid sequence substantially similar to that shown in FIG. 1 and in SEQ ID NO:2. Functionally equivalent Mch6 amino acid sequences similarly includes, for example, related, but different sequences so long as the different polypeptide exhibits at least one functional activity of Mch6. Such related, but different polypeptides include, for example, substitutions of conserved and nonessential amino acids. Fragments and functional domains of Mch6 are similarly included within the definition of the term and the claimed invention.

Therefore, it is understood that limited modifications may be made without destroying the biological function of the Mch6 polypeptide and that only a portion of the entire primary structure may be required in order to effect activity. For example, minor modifications of the Mch6 amino acid sequence (SEQ ID NO:2) that do not destroy their activity also fall within the definition of Mch6 and within the definition of the polypeptide claimed as such. Also within the definition of the claimed polypeptides are, for example, genetically engineered fragments of Mch6, either alone or fused to heterologous proteins such as fusion proteins that retain measurable enzymatic or other biological activity.

It is understood that minor modifications of primary amino acid sequence may result in polypeptides that have substantially equivalent or enhanced function as compared to the sequences set forth in FIG. 1 (SEQ ID NO:2). These modifications may be deliberate, as through site-directed mutagenesis, or may be accidental such as through mutation in hosts that are Mch6 producers. All of these modifications are included as long as Mch6 biological function is retained. Further, various molecules can be attached to Mch6, for example, other proteins, carbohydrates, lipids, or chemical moieties. Such modifications are included within the definition of an Mch6 polypeptide.

The invention provides a gene encoding Mch6, or fragment thereof. The invention also provides an isolated nucleic acid sequence encoding Mch6, or fragment thereof. The gene and nucleic acid sequences encode substantially the sequence as shown in SEQ ID NO:1. Fragments of the gene or nucleic acid sequence are provided that comprise single or double stranded nucleic acids having substantially the sequences shown in SEQ ID NO:1.

The Mch6 nucleic acid of the present invention was identified and isolated by a novel approach of searching a human database of expressed sequence tags (ESTs) under various stringencies to identify potentially new sequence fragments that may have homology to the ICE family of cysteine proteases. Previously these proteases were referred to as the ICE-family of proteases and thus the initial search criteria was directed to the ICE family of cell death proteases. However, with the recent identification of Mch4 and Mch5, the proteases have been reclassified into three subfamilies referred to herein as the Ced-like, ICE-like and Nedd2/ICH-1-like subfamilies of cell death proteases.

When searching for potential new sequences related to the ICE family of proteases, novel sequences are identified by their homology to the ICE family of cell death proteases. These novel sequences are then used to design primers for attempting PCR amplification and cloning of the actual cDNA. The second primer for the amplification is designed to encompass homologous regions in nucleic acid sequences that encode known ICE protease family members. In this specific case, the primer was directed to a sequence analogous to the GSWFI/GSWYI pentapeptide sequence that is conserved in a number of the ICE/Ced-3 family of proteases. The primer design should take into account the predicted strandedness of both the EST sequence primer and the known primer. Thus, only if the homology search and primer hybridization conditions are successfully determined will such an approach allow PCR amplification of a fragment of the putative novel protease cDNA.

Because searching a genetic data base will yield homologous sequence matches to any nucleotide sequence query, additional criteria must be used to identify the authentic ICE subfamily homolog from among the non-specific homology matches. ICE family members share the highest degree of homology in the active site and catalytically important amino acid residues. A given EST returned by the search may not include one of these highly homologous sites, but may only include a region within the protease with cryptic homology. Confirming an EST as a novel ICE protease involves translation of all the positive EST hits in three different reading frames and subsequent identification of conservative active site or catalytically important amino acid sequence motifs. Then, using conventional cDNA cloning, a full length cDNA of the putative novel protease can be obtained and 1) analyzed for overall structural homology to ICE family members, 2) recombinantly expressed and analyzed for cysteine protease activity, and 3) analyzed for the induction of programmed cell death by heterologous expression of the cDNA in appropriate cells.

In addition to the methods described above for isolating Mch6 encoding nucleic acids, alternative methods can similarly be employed. For example, using the teachings described herein, those skilled in the art can routinely isolate and manipulate Mch6 nucleic acids using methods well known in the art. All that is necessary is the sequence of the Mch6-encoding nucleic acid (FIG. 1 and SEQ ID NO:1) or its amino acid sequence (FIG. 1 and SEQ ID NO:2). Such methods include, for example, screening a cDNA or genomic library by using synthetic oligonucleotides, nucleic acid fragments or primers as hybridization probes. Alternatively, antibodies to the Mch6 amino acid sequence or fragments thereof can be generated and used to screen an expression library to isolate Mch6-encoding nucleic acids. Other binding reagents to an Mch6 polypeptide can similarly be used to isolate an Mch6 polypeptide having substantially the amino acid sequence shown in FIG. 1. Similarly, substrate reagents such as non-cleavable peptide analogs of cysteine proteases can be used to screen and isolate an Mch6 polypeptide.

In addition, recombinant DNA methods currently used by those skilled in the art include the polymerase chain reaction (PCR). When combined with the Mch6 nucleotide and amino acid sequences described herein, PCR allows reproduction of Mch6 encoding sequences. PCR can amplify desired sequences exponentially starting from as little as a single gene copy. The PCR technology is the subject matter of U.S. Pat. Nos. 4,683,195, 4,800,159, 4,754,065 and 4,683,202, all of which are incorporated by reference herein.

The above-described methods are known to those skilled in the art and are described, for example, in Sambrook et al., *Molecular Cloning: A Laboratory Manual*, Cold Spring Harbor Laboratory, NY (1992) and the various references cited therein and in Ansubel et al., *Current Protocols in Molecular Biology*, John Wiley and Sons, Baltimore, Md. (1989); and in Harlow et al., *Antibodies: A Laboratory Manual*, Cold Spring Harbor Laboratory, NY(1989). These references and the publications cited therein are hereby expressly incorporated herein by reference.

The invention provides an isolated Mch6 polypeptide comprising substantially the amino acid sequence as that shown in FIG. 1 (SEQ ID NO:2). Mch6 functional fragments are also provided. Specific examples of Mch6 functional fragment include, for example, the catalytic domain that contains the active site amino acid sequence QACGG (SEQ ID NO:78). When compared to the active site amino acid sequence of other ASCP family members, QACRG (SEQ ID NO:79) or QACQG (SEQ ID NO:80), this active site sequence is similar but differs at position 4 with Arg (R) substituted by Gly (G).

An isolated Mch6 polypeptide of the invention can be obtained by a variety of methods known within the art. For example, the isolated peptides can be purified by biochemical methods including affinity chromatography, for example. Affinity matrices for Mch6 isolation can be anti-Mch6 monoclonal or polyclonal antibodies prepared against the amino acid sequence shown in FIG. 1 (SEQ ID NO:2) or against fragments thereof such as synthetic peptides. Alternatively, substrate analogues or enzymatic inhibitors of Mch6 can similarly be used as affinity matrices to isolate substantially pure a Mch6 polypeptide of the invention.

An Mch6 polypeptide can also be produced by recombinant methods known to those skilled in the art. Recombinant Mch6 polypeptides include, for example, an amino acid sequence substantially the same as that shown in FIG. 1 (SEQ ID NO:2), as well as fusion proteins and fragments thereof. The Mch6-encoding nucleic acids can be cloned into the appropriate vectors for propagation, manipulation and expression. Such vectors are known or can be constructed by those skilled in the art and should contain all expression elements necessary for the transcription, translation, regulation, and if desired, sorting of the Mch6 polypeptides. The vectors can also be for use in either procaryotic or eucaryotic host systems so long as the expression and regulatory elements are compatible. One of ordinary skill in the art will know which host systems are compatible with a particular vector. The recombinant polypeptides produced can be isolated by the methods described above.

The invention further provides isolated large and small subunits of an Mch6 polypeptide. For example, the proMch6 polypeptide can be proteolytically cleaved by CPP32 or granzyme B to form a large and small subunit (Examples III and IV). In particular, CPP32 can cleave proMch6 into a large subunit having an approximate molecular weight of 37 kDa (p37) and a small subunit having an approximate molecular weight of 10 kDa (p10). Similarly, granzyme B can cleave proMch6 into a large subunit having an approximate molecular weight of 35 kDa (p35) and a small subunit having an approximate molecular weight of 12 kDa (p12). Moreover, other components of the apoptotic pathway can process Mch6 into a larger and a smaller cleavage product. Accordingly, the terms "large subunit" and "small subunit" will readily be understood to refer to any larger proteolytic cleavage product such as p37 or p35, and any smaller cleavage product such as p10 or 12, respectively.

Apoptosis plays a significant role in numerous pathological conditions in that programed cell death is either inhibited, resulting in increased cell survival, or enhanced, which results in the loss of cell viability. Examples of pathological conditions resulting from increased cell survival include cancers such as lymphomas, carcinomas and hormone-dependent tumors. Such hormone-dependent tumors include, for example, breast, prostate and ovarian cancer. Increased cell survival or apoptosis inhibition can also result in autoimmune diseases such as systemic lupus erythematosus and immune-mediated glomerulonephritis, as well as viral infections such as herpesvirus, poxvirus and adenovirus.

In contrast, apoptotic diseases where enhanced programed cell death is a prevalent cause generally includes, for example, degenerative disorders such as Alzheimer's disease, Parkinson's disease, amyotrophic lateral sclerosis, retinitis pigmentosa, and cerebellar degeneration. Other diseases associated with increased apoptosis include, for example, myelodysplastic syndromes such as aplastic anemia and ischemic injury, including myocardial infarction, stroke and reperfusion injury.

The Mch6-encoding nucleic acids and polypeptides of the invention can be used to diagnose, treat or reduce the severity of cell death-mediated diseases such as those described above as well as other diseases mediated by either increased or decreased programmed cell death. Additionally, the Mch6-encoding nucleic acids and polypeptides of the invention can be used to screen for pharmaceutical compounds and macromolecules that inhibit or promote Mch6-mediated apoptosis.

For example, the Mch6-encoding nucleic acids, polypeptides and functional fragments thereof can be used to diagnose or generate reagents to diagnose diseases mediated or characterized by programed cell death. Diagnosis can be by nucleic acid probe hybridization with Mch6-containing nucleotide sequences, antibody- or ligand-mediated detection with Mch6-binding agents, or by enzyme catalysis of detectable Mch6 substrates. Such methods are routine to those skilled in the art. Detection can be performed ex vivo, for example, by removing a cell or tissue sample from an individual exhibiting or suspected of exhibiting a cell death-mediated disease. Correlation of increased Mch6 expression or activity is indicative of diseases characterized by enhanced programmed cell death, whereas correlation of decreased Mch6 expression or activity is indicative of diseases characterized by the inhibition of programmed cell death.

The above Mch6 polypeptide can also be formulated into pharmaceutical compositions for treating cell death-mediated diseases characterized by increased cell survival and proliferation. Functional fragments and peptides such as the catalytic domain of Mch6 can similarly be formulated to treat such diseases.

Additionally, molecules that interact with Mch6 can also be used to induce Mch6-mediated apoptosis. Administration of Mch6 polypeptides and functional fragments thereof will induce apoptosis in treated cells and eliminate those cells characterized by increased cell survival or proliferation. Non-Mch6 polypeptides that do not directly act on Mch6 substrates but induce the activation of the Mch6 protease can similarly be administered to treat diseases characterized by increased cell survival and proliferation.

To be effective, the Mch6 polypeptide must be introduced into the cells by means characterized by increased cell survival. Introduction can be accomplished by a variety of means known within the art including, for example, lipid vesicles and receptor-mediated endocytosis. Targeting to the appropriate cell type can similarly be accomplished through conjugation to specific receptor ligands, specific target cell antibodies and the like.

The Mch6 polypeptide is administered by conventional methods in dosages that are sufficient to induce apoptosis in the cells characterized by increased cell survival or proliferation. Such dosages are known or can be easily determined by those skilled in the art. Administration can be accomplished, for example, by intravenous, interperitoneal or subcutaneous injection. Administration can be performed in a variety of different regimes that include single high dose administration, repeated small dose administration, or a combination of both. The administration will depend on the cell type, progression of the disease and overall health of the individual and will be known or can be determined by those skilled in the art.

In contrast to the induction of Mch6-mediated apoptosis to treat pathological conditions characterized by increased cell survival or proliferation, inhibitors of Mch6 can be used to treat diseases characterized by increased programmed cell death. Mch6 inhibitors include, for example, small molecules and organic compounds that bind and inactivate Mch6 protease activity by a competitive or noncompetitive-type mechanism, inhibitors of the conversion of inactive proMch6 into active Mch6 protease or other molecules that indirectly inhibit the Mch6 pathway. Such Mch6 inhibitors can include, for example, suicide inhibitors, anti-Mch6 antibodies and proteins, small peptidyl protease inhibitors, or small non-peptide organic molecule inhibitors. Specific examples of such inhibitors are described in Example II, and include substrate analogs such as tetrapeptide DEVD-CHO (Asp-Glu-Val-Asp-aldehyde; SEQ ID NO:81), DEVD-AMC (Asp-Glu-Val-Asp-aminomethylcoumarin; SEQ ID NO:82), YVAD-AMC (Tyr-Val-Ala-Asp-aminomethylcoumarin; SEQ ID NO:83), ZEVD-AMC (carbobenzoxy-Glu-Val-Asp-aminomethylcoumarin) and the cowpox virus protein Crm A. Mch6 inhibitors can be formulated in a medium that allows introduction into the desired cell type or can be attached to targeting ligands for introduction by cell-mediated endocytosis and other receptor-mediated events.

Mch6 inhibitors can also be used to treat or reduce the severity of diseases characterized by increased programmed cell death. In this regard, Mch6 large subunits that lack the active site QACGG (SEQ ID NO:78) can be used to bind the small subunit of Mch6 to prevent the formation of active protease complexes. Such a mechanism of dominant negative inhibition of Mch6 is similar to the dominant negative inhibition of Ich-$1_L$ by Ich-$1_S$. Subunits from other ASCPs can similarly be used as dominant/negative inhibitors of Mch6 activity and therefore be used to treat diseases mediated by programmed cell death. Such subunits should be selected so they bind either the p35 or p10 Mch6 polypeptide and prevent their assembly into active tetrameric protease complexes. Moreover, Mch6 subunits that have been modified to be catalytically inactive can also be used as dominant negative inhibitors of Mch6. Such modifications include, for example, mutation of the active site cysteine residue to include alanine or glycine, for example.

Mch6 substrate antagonists can similarly be used to treat or reduce the severity of diseases mediated by increased programmed cell death. Such substrate antagonists can bind to and inhibit cleavage by Mch6. Inhibition of substrate cleavage prevents commitment progression of programmed cell death. Substrate antagonists include, for example, ligands and small molecule compounds.

Mch6 inhibitors can be identified by incubating cells with a compound to be tested for inhibitory activity and then treated with a stimulus of apoptosis such as anti-Fas antibody, Fas ligand or staurosporin. Control samples in the absence of inhibitors that are subsequently treated with anti-Fas antibody undergo apoptosis and exhibit a rapid induction of ASCP activity. In contrast, samples in the presence of inhibitors reduce or negate ASCP activity compared to that in control samples.

Mch6 inhibitors can also be identified using Mch6-encoding nucleic acids and the Mch6 polypeptide of the invention in, for example, binding assays such as ELISA or RIA, or enzymatic assays using tetrapeptide substrates, such as DEVD-AMC (SEQ ID NO:82) and YVAD-AMC (SEQ ID NO:83). DEVD-AMC (SEQ ID NO:82) and YVAD-AMC (SEQ ID NO:83) represent cleavage sites for the poly(ADP-ribose)polymerase (PARP) and IL-l1β P1–P4 substrate tetrapeptides, respectively (Nicholson et al., *Nature* 376:37–43 (1995)).

The Mch6 polypeptide to be used in such assays can be obtained by, for example, in vitro translation, recombinant expression or biochemical procedures. Such and other methods are known within the art, and are illustrated in Example II. For example, recombinant Mch6 can be expressed by cloning Mch6 cDNA into a bacterial expression vector such as pET21b (Novagen Inc., Madison, Wis.). The Mch6 can then be expressed and purified using routine molecular biology methods known to those skilled in the art. A purified recombinant Mch6 protein can be used to measure hydrolysis rates for various substrates, such as DEVD-AMC (SEQ ID NO:82) and YVAD-AMC in a continuous fluorometric assay.

Using such an assay for Mch6 activity, various compounds can be screened for compounds that inhibit or enhance the expression of Mch6 protease activity. Such screening methods are known to those skilled in the art and can be performed by either in vitro or in vivo procedures. Such inhibitory molecules can be those contained in synthetic or naturally occurring compound libraries. A specific example is phage display peptide libraries where greater than $10^8$ peptide sequences can be screened in a single round of panning.

Treatment or reduction of the severity of cell death-mediated diseases can also be accomplished by introducing expressible nucleic acids encoding a Mch6 polypeptide or functional fragments thereof into cells characterized by such diseases. For example, elevated synthesis rates of Mch6 can be achieved by, for example, using recombinant expression vectors and gene transfer technology. Similarly, treatment or reduction of the severity of cell death-mediated diseases can also be accomplished by introducing and expressing antisense Mch6 nucleic acids to inhibit the Mch6 synthesis rate. Such methods are well known within the art and are described below with reference to recombinant viral vectors. Other vectors compatible with the appropriate targeted cell can accomplish the same goal and therefore can be substituted in the methods described herein in place of recombinant viral vectors.

Recombinant viral vectors are useful for in vivo expression of a desired nucleic acid because they offer advantages such as lateral infection and targeting specificity. Lateral infection is inherent in the life cycle of retroviruses and is the process by which a single infected cell produces many progeny virions that bud off and infect neighboring cells. The result is the rapid infection of a large area, most of which was not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Typically, viruses infect and propagate in specific cell types. Therefore, the targeting specificity of viral vectors utilizes this natural specificity to specifically introduce a desired gene into predetermined cell types. The vector to be used in the methods of the invention will depend on desired cell type to be targeted. For example, to treat neurodegenerative diseases by decreasing the Mch6 activity of affected neuronal cells, a vector should be used that is specific for cells of the neuronal cell lineage. Likewise, to treat diseases or pathological conditions of hematopoietic cells, a viral vector should be used that is specific for blood cells and their precursors, preferably for the specific type of hematopoietic cell. Moreover, such vectors can be modified with specific receptors or ligands and the like to modify or alter target specificity through receptor-mediated events. These modification procedures can be performed by, for example, recombinant DNA techniques or synthetic chemistry procedures. The specific type of vector will depend upon the intended application. The actual vectors are also known and readily available within the art or can be constructed by one skilled in the art using well known methodology.

Viral vectors encoding Mch6 nucleic acids or inhibitors of Mch6 such as antisense nucleic acids can be administered in several ways to obtain expression of such sequences and therefore either increase or decrease the activity of Mch6 in the cells affected by the disease or pathological condition. If viral vectors are used, for example, the procedure can take advantage of their target specificity and consequently need not be administered locally at the diseased site. However, local administration can provide a quicker and more effective treatment. Administration can also be performed by, for example, intravenous or subcutaneous injection into the subject. Injection of the viral vectors into the spinal fluid can also be used as a mode of administration, especially in the case of neurodegenerative diseases. Following injection, the viral vectors will circulate until they recognize host cells with the appropriate target specificity for infection.

As described above, one mode of administration of Mch6-encoding vectors can be by direct inoculation locally at the site of the disease or pathological condition. Local administration is advantageous because there is no dilution effect and therefore a smaller dose is can be sufficient to achieve Mch6 expression in a majority of the targeted cells. Additionally, local inoculation can alleviate the targeting requirement associated with other forms of administration because a vector can be used that infects all cells in the inoculated area. If expression is desired in only a specific subset of cells within the inoculated area, then promoter and expression elements that are specific for the desired subset can be used to accomplish this goal. Such non-targeting vectors can be, for example, viral vectors, viral genomes, plasmids, phagemids and the like. Transfection vehicles such as liposomes can be used to introduce the non-viral vectors described above into recipient cells within the inoculated area. Such transfection vehicles are known by one skilled within the art. Alternatively, however, non-targeting vectors can be administered directly into a tissue of any individual. Such methods are known within the art and are described by, for example, Wolff et al. (*Science* 247:1465–1468 (1990)).

Additional features can be added to the vectors to ensure safety and/or enhance therapeutic efficacy. Such features include, for example, markers that can be used to negatively select against cells infected with the recombinant virus. An example of such a negative selection marker is the TK gene described above, which confers sensitivity to the antibiotic gancyclovir. Infection can therefore be controlled by negative selection because it provides inducible suicide through the addition of an antibiotic. Such protection ensures that if, for example, mutations arise that produce mutant forms of Mch6, dysfunction of apoptosis will not occur.

It is understood that modifications that do not substantially affect the activity of the various embodiments of this invention are also included within the definition of the invention provided herein. Accordingly, the following examples are intended to illustrate but not limit the present invention.

EXAMPLE I

Cloning and Characterization of Mch6

This Example shows the cloning, sequence analysis and tissue distribution of Mch6. The results described herein indicate that Mch6 is a novel member of the ICE family of aspartate-specific cysteine proteases (ASCPs).

To identify potentially novel members of the ICE family of ASCPs, an approach combining information from the GenBank database of human expressed sequence tags (ESTs) and PCR was employed (see Fernandes-Alnemri et al., *Cancer Res.* 55:2737–2742 (1995); Fernandes-Alnemri et al., *Cancer Res.* 55:6045–6052 (1995)). Initially, a search of GenBank ESTs for sequences related to CPP32 and Mch2 identified a short EST sequence, which was used to derive a PCR primer to clone related cDNAs. The EST sequence was identified as accession number T97582 and was used to design primer Mch6-pr1, having the nucleotide sequence CTCAACGTACCAGGAGCC (SEQ ID NO:3). A 10 $\mu$l aliquot of human Jurkat $\lambda$ Uni-Zap™ XR cDNA library (Fernandes-Alnemri et al., *J. Biol. Chem.* 269:30761–30764 (1994)) containing approximately $10^8$ pfu was denatured at 99° C. for 5 min. and used as a template for PCR amplification with the above Mch6-pr1 primer and a T3 vector-specific primer (Stratagene).

A 10 $\mu$l aliquot of the primary amplification product was then used as a template for a secondary PCR amplification with primer Mch6-pr2, having nucleotide sequence CCTGGGAAAGTAGAGTAGG (SEQ ID NO:4), which was also derived from EST sequence T97582, and the SK-Zap vector-specific primer located downstream of the T3 primer, having nucleotide sequence CAGGAATTCG-GCACGAG (SEQ ID NO:5). The secondary amplification products were cloned into a SmaI-cut pBluescript II KS$^+$ vector. The partial cDNA was then excised from the vector, radiolabeled and used to screen the original Jurkat $\lambda$ Uni-Zap™ XR cDNA library for full length cDNA clones. Positive $\lambda$ clones were purified, rescued into the pBluescript II SK$^-$ plasmid vector and sequenced.

The screen of the full length Jurkat $\lambda$ Uni-Zap™ XR cDNA library resulted in the isolation of an approximately 2 kb cDNA clone. This cDNA contains an open reading frame of 1248 bp (SEQ ID NO:1) that encodes a 416-amino acid protein, named proMch6 (SEQ ID NO:2). As shown in FIG. 1, proMch6 is a polypeptide of 479 amino acid residues with a predicted molecular mass of approximately 46.2 kDa.

Shown in FIG. 2 is a multiple amino acid sequence alignment of relatively conserved regions within the ASCPs. These regions include, for example, the relatively conserved active site pentapeptide sequence QACRG (SEQ ID NO:79), residues involved in catalysis, residues that bind the substrate-carboxylate of P1 Asp, residues adjacent to the substrate P2–P4 amino acids and the known and potential processing sites between the small and large subunits. Sequence alignment of all known ASCPs revealed that Mch6 belongs to the Ced-3-like subfamily of ASCPs. Briefly, previously identified ASCPs can be divided phylogenetically into three subfamilies. The Ced-3-like ASCP subfamily includes Ced-3, CPP32, Mch2, Mch3, Mch4 and Mch5 (noncontiguous SEQ ID NOs:6–11). The ICE-like ASCP subfamily includes ICE, TX (noncontiguous ICH-2, ICErel-II, Mih1) and ICErelIII (noncontiguous SEQ ID NOs:12–14). The NEDD-like subfamily includes ICH-1 (noncontiguous SEQ ID NO:15) and its mouse counterpart NEDD2. Within the Ced-3-like subfamily, Mch6 shows the highest homology to CPP32 approximately 37% identity, 57% similarity).

Mch6 is also structurally similar to other ASCPs. The mature Mch6 could be derived from the precursor proenzyme by cleavage at highly conserved Asp residues (Asp315 and Asp330) located between the two subunits. One difference between this enzyme and other family members, however, is that the fourth residue in its active site pentapeptide sequence QACGG (SEQ ID NO:78) is a Gly instead of Arg or Gln (FIG. 1).

Study of the known crystal structure of ICE has revealed that His237, Gly238 and Cys285 are involved in catalysis, while Arg179, Gln283, Arg341 and Ser347 are involved in binding the carboxylate side chain of the substrate P1 aspartate (Walker et al., Cell 78:343–352 (1994); Wilson, et al., Nature 370:270–275 (1994)). All these residues are identical in all family members except in Mch5, where there is a Ser to Thr conservative substitution for the residue corresponding to Ser347 of ICE (FIG. 2). Another Ser to Thr conservative substitution can also be seen in Mch4 in the region corresponding to Ser236 of ICE, which is one of the residues that participates in binding the substrate P2–P4 residues. Other residues that might participate in binding the substrate P2–P4 residues are not widely conserved, suggesting that they may determine substrate specificity.

In addition to the above sequence analysis, further characterization of Mch6 was also performed by analyzing its tissue distribution. This analysis was performed by RNA blot analysis of poly A+ RNA isolated from different human tissues (Fernandes-Alnemri et al., Cancer Res. 55:6045–6052 (1995)). Briefly, tissue distribution analysis of Mch6 mRNA was performed on northern blots prepared by Clontech (San Diego, Calif.) containing 2 μg/lane of poly A+ RNA from each tissue of origin. A radioactive Mch6 riboprobe was prepared using Mch6 cDNA as a template for T7 RNA polymerase in the presence of $[\alpha^{32}P]$ATP. The blots were hybridized, washed and then visualized by autoradiography.

The proMch6 riboprobe detected three major mRNA species (approximately 1.0 kb, approximately 2.4 kb and approximately 4.4 kb) in most human tissues. Highest expression was seen in the heart, and moderate expression in the liver, skeletal muscle and pancreas. Lowest expression was observed in the other tissues tested. The presence of multiple mRNA species has been observed with ICE and is suggestive of alternative splicing or polyadenylation (Cerretti et al., Science 256:97–100 (1992)).

To determine if Mch6 exhibits apoptotic activity, Sf9 baculovirus cells are used. Briefly, Sf9 cells are infected with recombinant baculoviruses encoding full length Mch6, full length CPP32 or truncated variants of Mch6 or CPP32, separately or in various combinations. Cells are then examined microscopically for morphological signs of apoptosis such as blebbing of the cytoplasmic membrane, condensation of nuclear chromatin or release of small apoptotic bodies. In addition, the genomic DNA is examined for internucleosomal DNA cleavage.

EXAMPLE II

Kinetic Parameters of Mch6

This Example characterizes the protease activity and substrate specificity of the ASCP Mch6.

The kinetic properties of bacterially expressed recombinant Mch6 were determined using the tetrapeptide substrates DEVD-AMC (SEQ ID NO:82), ZEVD-AMC and YVAD-AMC (SEQ ID NO:83) in a continuous fluorometric assay (Table I). The DEVD-AMC (SEQ ID NO:82) and ZEVD-AMC represent the cleavage site for poly(ADP-ribose) polymerase (PARP). The YVAD-AMC (SEQ ID NO:83) represents the cleavage site for IL-L1β P1–P4 substrate tetrapeptide (Nicholson et al., Nature 376:37–43 (1995)). Briefly, Mch6 cDNA was cloned in-frame into bacterial expression vector pET21b (Novagen Inc., Madison, Wis.). The expression vector was constructed and expressed as a 6His-C terminal tagged protein in host bacterial strain BL21(DE3) using routine molecular biology methods known to those skilled in the art. After induction with IPTG, bacterial extracts were prepared from E. coli expressing the recombinant proteins. The extracts were then purified on a a $Ni^{++}$ affinity column.

The purified Mch6 protein was then used for further enzymatic analyses. The activity of Mch6 was measured using bacterial lysates prepared with ICE buffer (25 mM HEPES, 1 mM EDTA, 5 mM DTT, 0.1% CHAPS, 10% sucrose, pH 7.5) at room temperature (24–25° C.). The $K_i$ of DEVD-CHO (SEQ ID NO:81) was determined from the hydrolysis rate of 50 μM DEVD-AMC (SEQ ID NO:82) following a 30 min preincubation of the enzyme with DEVD-CHO (SEQ ID NO:81).

TABLE I

Kinetic Parameters of Mch6

| Parameter | Value |
| --- | --- |
| $K_m$ (DEVD-AMC) | 10 μM |
| $K_i$ (DEVD-CHO) | <10 nM |
| $V_{max}/K_m$ (DEVD-AMC) | 100 |
| $V_{max}/K_m$ (ZEVD-AMC) | 2.7 |
| $V_{max}/K_m$ (YVAD-AMC) | <0.1 |

As shown above in Table I, Mch6 is potently inhibited by the DEVD-CHO peptide ($K_i$<10 nM). Mch6 also shows a greater than 1000-fold preference for the CPP32-like substrate DEVD-AMC (SEQ ID NO:82) compared to the ICE-like substrate YVAD-AMC (SEQ ID NO:83), by comparing $V_{max}/K_m$ for each substrate. These kinetic parameters indicates that Mch6 is more related to the CPP32-like ASCPs than to the ICE-like enzymes.

EXAMPLE III

CPP32 Processes proMch6 in vitro

This example shows that CPP32 processes proMch6 at the Asp330 site to yield a large and a small cleavage product.

Wild type proMch6 contains a potential CPP32 cleavage site at the $^{327}$DQLD-A$^{331}$ site (SEQ ID NO:85), which is similar to the DEVD-G site (SEQ ID NO:86) in PARP and the DVVD-N site (SEQ ID NO:87) in proMch2 (Nicholson et al., Nature 376:37–43(1995)). These similarities suggest that CPP32 can also process proMch6 as well.

To provide proMch6 as a potential processing substrate, proMch6 cDNA was transcribed and translated in vitro in the presence of $^{35}$S-methionine using coupled transcription/translation TNT kit according to the manufacturer's recommendations (Promega, Madison Wis.). Two microliters of the translation reaction were incubated with purified enzymes (100–200 ng) or bacterial lysates in ICE buffer (25 mM HEPES, 1 mM EDTA, 5 mM DTT, 0.1% CHAPS, 10% sucrose, pH 7.5), in a final volume of 10 μl. The reaction was incubated at 37° C. for 1–2 hours and the resulting translation products were analyzed by Tricine-SDS-PAGE and autoradiography.

To determine the ability of CPP32 to process proMch6, proMch6 from in vitro translation was incubated for various times with purified recombinant human CPP32 and then analyzed by Tricine-SDS-PAGE and autoradiography. The CPP32 was obtained by expression in bacteria, assayed for activity and purified on a $Ni^{+2}$ affinity resin (Fernandes-Alnemri et al., *Cancer Res.* 55:2737–2742; Fernandes-Alnemri et al., *Cancer Res.* 55:6045–6052 (1995)).

Analysis of the time course revealed that CPP32 cleaves proMch6 at one site to generate two cleavage products of approximately 37 kDa or p37 and approximately 10 kDa or p10. The sizes of the products were consistent with cleavage at the $^{327}$DQLD-A$^{331}$ site (SEQ ID NO:85), which contains Asp330. Products were initially detected within the first 15 minutes. Longer incubation resulted in decreased intensity of the full length 46 kDa band and increased intensity of the p37 and p10 products. Prolonged incubation did not result in significant processing of the p37 product. This result indicates that CPP32 cleaves preferentially at only one site within proMch6.

The CPP32 processing site was confirmed by constructing and analyzing mutants of proMch6. Briefly, potential processing sites were mutated by site-directed mutagenesis using overlapping PCR mutagenic oligonucleotides. The resulting PCR products were subcloned in pBluescript II KS$^+$ vector under the T7 promoter and their sequences were verified by DNA sequencing. In particular, Asp315 of proMch6 was mutated to Ala for one mutant and Asp330 was mutated to Ala for another mutant.

As with the wild type proMch6, the Asp315 mutant was processed by CPP32 to generate the p37 and p10 products. In contrast, CPP32 failed to process the Asp330 mutant. These results show that CPP32 processes proMch6 at the Asp330 site.

EXAMPLE IV

Granzyme B Cleaves proMch6 Preferentially at the PEPD-A site (SEQ ID NO:84)

This example shows that granzyme B cleaves proMch6 at two sites, with a preference for cleaving at the $^{312}$PEPD-A$^{316}$ site (SEQ ID NO:84).

Granzyme B can induce apoptosis in target cells by activation of ASCPs. The ability of granzyme B to process several members of the ASCP family has now been demonstrated (Fernandes-Alnemri et al., *Proc. Natl. Acad. Sci. USA* 93:7464–7469 (1996)). To test whether granzyme B can process proMch6, $^{35}$S-labeled proMch6 was prepared and incubated with granzyme B and then analyzed by Tricine-SDS-PAGE and autoradiography, as described in Example III. The granzyme B used for these assays was purified by immunopurification from human natural killer cell lysates using granzyme B-specific monoclonal antibody (Trapani et al., *Biochem. Biophys. Res. Commun.* 195:910–920 (1993); Trapani et al., *J. Biol. Chem.* 269:18359–18365 (1994)). The results indicate that granzyme B cleaves proMch6 preferentially at one site to generate a large product of approximately 35 kDa (p35) and a small product of approximately 12 kDa (p12).

In comparison with the products of CPP32 processing described in Example III, the large granzyme B product (p35) migrates faster than the large CPP32 product (p37), indicating that the enzymes cleave at two different sites. The granzyme B cleavage site is in the N-terminal direction of the CPP32 cleavage site and it is most likely to be Asp315 within the $^{312}$PEPD-A$^{316}$ site (SEQ ID NO:84).

The location of the granzyme B cleavage sites were confirmed by using proMch6 mutants as described in Example III. Unlike CPP32, granzyme B cleaved the Asp330 mutant to generate p35 and p12 products. When granzyme B was assayed with the Asp315 mutant, the p35 and p12 products were absent. This result indicated that granzyme B was unable to process the $^{312}$PEPD-A$^{316}$ site (SEQ ID NO:84). Granzyme B did cleave the Asp315 mutant at the $^{327}$DQLD-A$^{331}$ site (SEQ ID NO:85) to generate faint p37 and p10 products, albeit inefficiently. A double mutant form of proMch6 at Asp315 and Asp330, which was prepared by site-directed mutagenesis as described in Example III, completely blocked processing of proMcH6 by granzyme B and CPP32. These results show that granzyme B processes proMch6 at Asp315 and Asp330 with preference for Asp315 over Asp330.

EXAMPLE V

Activation of proCPP32 by Granzyme B in a Cell Lysate Lead to Processing of proMch6 at Asp315 and Asp330 Simultaneously This example shows that activation of proCPP32 by granzyme B in cell lysate results in cleavage of proMch6 at two sites simultaneously.

As described in Examples III and IV, CPP32 and granzyme B process proMch6 at two different sites. To determine whether granzyme B can process proCPP32 into CPP32, followed by simultaneous processing of proMch6 by granzyme B and CCP32, $^{35}$S-labeled proMch6 was mixed with cell extract from 697 lymphocyte cell line and then incubated with granzyme B.

The products of the incubated reaction were analyzed at different time points by western blotting to detect activation of endogenous proCPP32. The western blots used a rabbit polyclonal anti-human CPP32 antibody, which was raised against recombinant p20 subunit (amino acids 1–175) of human CPP32. Autoradiography was also used to detect processing of proMch6. The p20/p19 doublet of mature CPP32 was detected in less than 15 minutes, simultaneously with the disappearance of the 32 kDa proCPP32. Subsequently, the p20 product was autocatalytically processed to the p19. In the presence of the DEVD-CHO (SEQ ID NO:81) inhibitor, only the p20 could be detected due to the inhibition of CPP32 under these conditions.

Autoradiographic analysis of the same samples revealed a time-dependent processing of proMch6 to the p35 (granzyme B product) and p37 (CPP32 product) bands. Also detectable was the p12/p10 band. When CPP32 was inhibited by the DEVD-CHO (SEQ ID NO:81), only the granzyme B-generated p35 and p12 bands were detected.

The above results indicate that the p37, p35, p12 and p10 products are produced in cells undergoing granzyme B-mediated apoptosis. This interpretation is based on the fact that cell lysates contain all the cytoplasmic components necessary for apoptosis (Trapani et al., *Biochem. Biophys. Res. Commun.* 195:910–920 (1993); Martin, et al., *EMBO J.* 14:5191–5200 (1995); Enari et al., *EMBO J.* 14:5201–5208 (1995)). Therefore, the mature Mch6 enzyme is derived from the proenzyme by cleavage at Asp315 and Asp330 to generate the large (p35) and small (p10) subunits, as shown in FIG. 3. Due to the lack of evidence of efficient processing in the prodomain in cell lysates, these results indicate that the p35 is the large subunit and p10 is the small subunit of mature Mch6. Moreover, these results further show that activation of proCPP32 by granzyme B in cell lysate results in cleavage of proMch6 at two sites simultaneously.

Throughout this application, various publications are referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. An isolated nucleic acid sequence encoding Mch6 comprising the sequence shown in SEQ ID NO:1.

2. An isolated nucleic acid sequence encoding a Mch6 of SEQ ID NO:2.

* * * * *

SEQUENCE LISTING (1) GENERAL INFORMATION:

(iii) NUMBER OF SEQUENCES: 87

(2) INFORMATION FOR SEQ ID NO:1:

(i) SEQUENCE CHARACTERISTICS:
      (A) LENGTH: 1251 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1251

(xi) SEQUENCE DESCRIPTION: SEQ ID NO:1:

```
ATG GAC GAA GCG GAT CGG CGG CTC CTG CGG CGG TGC CGG CTG CGG CTG      48
Met Asp Glu Ala Asp Arg Arg Leu Leu Arg Arg Cys Arg Leu Arg Leu
 1               5                  10                  15

GTG GAA GAG CTG CAG GTG GAC CAG CTC TGG GAC GCC CTG CTG AGC AGC      96
Val Glu Glu Leu Gln Val Asp Gln Leu Trp Asp Ala Leu Leu Ser Ser
                20                  25                  30

GAG CTG TTC AGG CCC CAT ATG ATC GAG GAC ATC CAG CGG GCA GGC TCT     144
Glu Leu Phe Arg Pro His Met Ile Glu Asp Ile Gln Arg Ala Gly Ser
            35                  40                  45

GGA TCT CGG CGG GAT CAG GCC AGG CAG CTG ATC ATA GAT CTG GAG ACT     192
Gly Ser Arg Arg Asp Gln Ala Arg Gln Leu Ile Ile Asp Leu Glu Thr
        50                  55                  60

CGA GGG AGT CAG GCT CTT CCT TTG TTC ATC TCC TGC TTA GAG GAC ACA     240
Arg Gly Ser Gln Ala Leu Pro Leu Phe Ile Ser Cys Leu Glu Asp Thr
 65                  70                  75                  80

GGC CAG GAC ATG CTG GCT TCG TTT CTG CGA ACT AAC AGG CAA GCA GCA     288
Gly Gln Asp Met Leu Ala Ser Phe Leu Arg Thr Asn Arg Gln Ala Ala
                85                  90                  95

AAG TTG TCG AAG CCA ACC CTA GAA AAC CTT ACC CCA GTG GTG CTC AGA     336
Lys Leu Ser Lys Pro Thr Leu Glu Asn Leu Thr Pro Val Val Leu Arg
            100                 105                 110

CCA GAG ATT CGC AAA CCA GAG GTT CTC AGA CCG GAA ACA CCC AGA CCA     384
Pro Glu Ile Arg Lys Pro Glu Val Leu Arg Pro Glu Thr Pro Arg Pro
        115                 120                 125

GTG GAC ATT GGT TCT GGA GGA TTT GGT GAT GTC GGT GCT CTT GAG AGT     432
Val Asp Ile Gly Ser Gly Gly Phe Gly Asp Val Gly Ala Leu Glu Ser
    130                 135                 140

TTG AGG GGA AAT GCA GAT TTG GCT TAC ATC CTG AGC ATG GAG CCC TGT     480
Leu Arg Gly Asn Ala Asp Leu Ala Tyr Ile Leu Ser Met Glu Pro Cys
145                 150                 155                 160

GGC CAC TGC CTC ATT ATC AAC AAT GTG AAC TTC TGC CGT GAG TCC GGG     528
Gly His Cys Leu Ile Ile Asn Asn Val Asn Phe Cys Arg Glu Ser Gly
                165                 170                 175
```

```
CTC CGC ACC CGC ACT GGC TCC AAC ATC GAC TGT GAG AAG TTG CGG CGT    576
Leu Arg Thr Arg Thr Gly Ser Asn Ile Asp Cys Glu Lys Leu Arg Arg
        180                 185                 190

CGC TTC TCC TCG CCG CAT TTC ATG GTG GAG GTG AAG GGC GAC CTG ACT    624
Arg Phe Ser Ser Pro His Phe Met Val Glu Val Lys Gly Asp Leu Thr
            195                 200                 205

GCC AAG AAA ATG GTG CTG GCT TTG CTG GAG CTG GCG CAG CAG GAC CAC    672
Ala Lys Lys Met Val Leu Ala Leu Leu Glu Leu Ala Gln Gln Asp His
        210                 215                 220

GGT GCT CTG GAC TGC TGC GTG GTG GTC ATT CTC TCT CAC GGC TGT CAG    720
Gly Ala Leu Asp Cys Cys Val Val Val Ile Leu Ser His Gly Cys Gln
225                 230                 235                 240

GCC AGC CAC CTG CAG TTC CCA GGG GCT GTC TAC GGC ACA GAT GGA TGC    768
Ala Ser His Leu Gln Phe Pro Gly Ala Val Tyr Gly Thr Asp Gly Cys
            245                 250                 255

CCT GTG TCG GTC GAG AAG ATT GTG AAC ATC TTC AAT GGG ACC AGC TGC    816
Pro Val Ser Val Glu Lys Ile Val Asn Ile Phe Asn Gly Thr Ser Cys
        260                 265                 270

CCC AGC CTG GGA GGA AAG CCC AAG CTC TTT TTC ATC CAG GCC TGT GGT    864
Pro Ser Leu Gly Gly Lys Pro Lys Leu Phe Phe Ile Gln Ala Cys Gly
            275                 280                 285

GGG GAG CAG AAA GAC CAT GGG TTT GAG GTG GCC TCC ACT TCC CCT GAA    912
Gly Glu Gln Lys Asp His Gly Phe Glu Val Ala Ser Thr Ser Pro Glu
        290                 295                 300

GAC GAG TCC CCT GGC AGT AAC CCC GAG CCA GAT GCC ACC CCG TTC CAG    960
Asp Glu Ser Pro Gly Ser Asn Pro Glu Pro Asp Ala Thr Pro Phe Gln
305                 310                 315                 320

GAA GGT TTG AGG ACC TTC GAC CAG CTG GAC GCC ATA TCT AGT TTG CCC   1008
Glu Gly Leu Arg Thr Phe Asp Gln Leu Asp Ala Ile Ser Ser Leu Pro
            325                 330                 335

ACA CCC AGT GAC ATC TTT GTG TCC TAC TCT ACT TTC CCA GGT TTT GTT   1056
Thr Pro Ser Asp Ile Phe Val Ser Tyr Ser Thr Phe Pro Gly Phe Val
        340                 345                 350

TCC TGG AGG GAC CCC AAG AGT GGC TCC TGG TAC GTT GAG ACC CTG GAC   1104
Ser Trp Arg Asp Pro Lys Ser Gly Ser Trp Tyr Val Glu Thr Leu Asp
            355                 360                 365

GAC ATC TTT GAG CAG TGG GCT CAC TCT GAA GAC CTG CAG TCC CTC CTG   1152
Asp Ile Phe Glu Gln Trp Ala His Ser Glu Asp Leu Gln Ser Leu Leu
        370                 375                 380

CTT AGG GTC GCT AAT GCT GTT TCG GTG AAA GGG ATT TAT AAA CAG ATG   1200
Leu Arg Val Ala Asn Ala Val Ser Val Lys Gly Ile Tyr Lys Gln Met
385                 390                 395                 400

CCT GGT TGC TTT AAT TTC CTC CGG AAA AAA CTT TTC TTT AAA ACA TCA   1248
Pro Gly Cys Phe Asn Phe Leu Arg Lys Lys Leu Phe Phe Lys Thr Ser
            405                 410                 415

TAA                                                               1251
```

(2) INFORMATION FOR SEQ ID NO:2:

(i) SEQUENCE CHARACTERISTICS:
        (A) LENGTH: 416 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Glu Ala Asp Arg Arg Leu Leu Arg Arg Cys Arg Leu Arg Leu
 1               5                  10                  15

Val Glu Glu Leu Gln Val Asp Gln Leu Trp Asp Ala Leu Leu Ser Ser
                20                  25                  30
```

```
Glu Leu Phe Arg Pro His Met Ile Glu Asp Ile Gln Arg Ala Gly Ser
        35                  40                  45

Gly Ser Arg Arg Asp Gln Ala Arg Gln Leu Ile Asp Leu Glu Thr
50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
            115                 120                 125

Val Asp Ile Gly Ser Gly Gly Phe Gly Asp Val Gly Ala Leu Glu Ser
        130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Pro His Phe Met Val Glu Val Lys Gly Asp Leu Thr
        195                 200                 205

Ala Lys Lys Met Val Leu Ala Leu Leu Glu Leu Ala Gln Gln Asp His
        210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415
```

(2) INFORMATION FOR SEQ ID NO:3:

(i) SEQUENCE CHARACTERISTICS:
        (A) LENGTH: 18 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:3:

CTCAACGTAC CAGGAGCC                                                                  18

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CCTGGGAAAG TAGAGTAGG                                                                 19

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CAGGAATTCG GCACGAG                                                                   17

(2) INFORMATION FOR SEQ ID NO:6:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:6:

Arg Thr Arg Thr Gly Ser Leu Ser His Gly Cys Gln Phe Ile Gln Ala
1               5                   10                  15

Cys Gly Gly Glu Gln Pro Glu Pro Asp Ala Asp Gln Leu Asp Ala Gly
            20                  25                  30

Phe Val Ser Trp Arg Asp Pro Lys Ser Gly Ser Trp Tyr Val
        35                  40                  45

(2) INFORMATION FOR SEQ ID NO:7:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:7:

Arg Asp Arg Asn Gly Thr Leu Ser His Gly Asp Lys Phe Ile Gln Ala
1               5                   10                  15

Cys Gln Gly Asp Asn Val Glu Thr Asp Ser Asn Cys Val Ser Tyr Arg
            20                  25                  30

Asn Pro Ala Glu Gly Thr Trp Tyr Ile 35                  40

(2) INFORMATION FOR SEQ ID NO:8:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:8:

Lys Asp Arg Gln Gly Thr Leu Thr His Gly Arg Phe Phe Ile Gln Ala
1               5                   10                  15

Cys Gln Gly Glu Glu Ile Glu Ala Asp Ala Gly Tyr Val Ser Phe Arg
            20                  25                  30

His Val Glu Glu Gly Ser Trp Tyr Ile
        35                  40

(2) INFORMATION FOR SEQ ID NO:9:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:9:

Gly Val Arg Asn Gly Thr Leu Ser His Gly Glu Glu Phe Ile Gln Ala
1               5                   10                  15

Cys Arg Gly Thr Glu Ile Gln Ala Asp Ser Gly Tyr Tyr Ser Trp Arg
            20                  25                  30

Ser Pro Gly Arg Gly Ser Trp Phe Val
        35                  40

(2) INFORMATION FOR SEQ ID NO:10:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:10:

Pro Glu Arg Arg Gly Thr Leu Ser His Gly Glu Gly Ile Ile Gln Ala
1               5                   10                  15

Cys Arg Gly Asn Gln Asp Val Val Asp Asn Thr Glu Val Asp Ala Gly
            20                  25                  30

Tyr Tyr Ser His Arg Glu Thr Val Asn Gly Ser Trp Tyr Ile
        35                  40                  45

(2) INFORMATION FOR SEQ ID NO:11:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:11:

Thr Ser Arg Ser Gly Thr Leu Ser His Gly Glu Glu Ile Ile Gln Ala
1               5                   10                  15

```
Cys Arg Gly Thr Glu Ile Glu Thr Asp Ser Gly Tyr Tyr Ser Trp Arg
            20                  25                  30

Asn Ser Lys Asp Gly Ser Trp Phe Ile
            35                  40
```

(2) INFORMATION FOR SEQ ID NO:12:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:12:

```
Pro Thr Arg Asn Gly Thr Leu Ser His Gly Glu Phe Val Gln Ala
1               5                   10                  15

Cys Arg Gly Glu Arg Asp Ser Val Asp Gly Gln Tyr Val Ser Trp Arg
            20                  25                  30

Asn Ser Ala Arg Gly Ser Trp Phe Ile
            35                  40
```

(2) INFORMATION FOR SEQ ID NO:13:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:13:

```
Pro Arg Arg Thr Gly Ala Met Ser His Gly Ile Arg Ile Ile Gln Ala
1               5                   10                  15

Cys Arg Gly Asp Ser Trp Phe Lys Asp Ser Phe Glu Asp Asp Ala Asp
            20                  25                  30

Asn Val Ser Trp Arg His Pro Thr Met Gly Ser Val Phe Ile
            35                  40                  45
```

(2) INFORMATION FOR SEQ ID NO:14:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:14:

```
Pro Pro Arg Asn Gly Ala Met Ser His Gly Ile Leu Ile Val Gln Ala
1               5                   10                  15

Cys Arg Gly Ala Asn Trp Val Lys Asp Ser Leu Glu Glu Asp Ala His
            20                  25                  30

Asn Val Ser Trp Arg Asp Ser Thr Met Gly Ser Ile Phe Ile
            35                  40                  45
```

(2) INFORMATION FOR SEQ ID NO:15:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:15:

Pro Ala Arg Asn Gly Ala Met Ser His Gly Ile Leu Ile Val Gln Ala
1               5                   10                  15

Cys Arg Gly Glu Lys Trp Val Arg Asp Ser Leu Glu Ala Asp Ser His
                20                  25                  30

Asn Val Ser Trp Arg Asp Arg Thr Arg Gly Ser Ile Phe Ile
            35                  40                  45

(2) INFORMATION FOR SEQ ID NO:16:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:16:

Glu Phe Arg Ser Gly Gly Leu Ser His Gly Val Glu Phe Ile Gln Ala
1               5                   10                  15

Cys Arg Gly Asp Glu Asp Gln Gln Asp Gly Glu Glu Ser Asp Ala Gly
                20                  25                  30

Thr Ala Ala Met Arg Asn Thr Lys Arg Gly Ser Trp Tyr Ile
            35                  40                  45

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Arg Thr Arg Thr Gly Ser
1               5

(2) INFORMATION FOR SEQ ID NO:18:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:18:

Leu Ser His Gly Cys Gln
1               5

(2) INFORMATION FOR SEQ ID NO:19:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:19:

Phe Ile Gln Ala Cys Gly Gly Glu Gln
1               5

(2) INFORMATION FOR SEQ ID NO:20:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:20:

```
Pro Glu Pro Asp Ala
1               5
```

(2) INFORMATION FOR SEQ ID NO:21:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:21:

```
Asp Gln Leu Asp Ala
1               5
```

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:22:

```
Gly Phe Val Ser Trp Arg Asp Pro Lys Ser Gly Ser Trp Tyr Val
1               5                   10                  15
```

(2) INFORMATION FOR SEQ ID NO:23:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:23:

```
Arg Asp Arg Asn Gly Thr
1               5
```

(2) INFORMATION FOR SEQ ID NO:24:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:24:

```
Leu Ser His Gly Asp Lys
1               5
```

(2) INFORMATION FOR SEQ ID NO:25:

(i) SEQUENCE CHARACTERISTICS:

(A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:25:

Phe Ile Gln Ala Cys Gln Gly Asp Asn
1               5

(2) INFORMATION FOR SEQ ID NO:26:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:26:

Val Glu Thr Asp Ser
1               5

(2) INFORMATION FOR SEQ ID NO:27:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:27:

Asn Cys Val Ser Tyr Arg Asn Pro Ala Glu Gly Thr Trp Tyr Ile
1               5                   10                  15

(2) INFORMATION FOR SEQ ID NO:28:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:28:

Lys Asp Arg Gln Gly Thr
1               5

(2) INFORMATION FOR SEQ ID NO:29:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:29:

Leu Thr His Gly Arg Phe
1               5

(2) INFORMATION FOR SEQ ID NO:30:

(i) SEQUENCE CHARACTERISTICS:
        (A) LENGTH: 9 amino acids
        (B) TYPE: amino acid
        (D) TOPOLOGY: linear

```
    (ii) MOLECULE TYPE: peptide (xi) SEQUENCE DESCRIPTION: SEQ ID NO:30:

Phe Ile Gln Ala Cys Gln Gly Glu Glu
1               5

(2) INFORMATION FOR SEQ ID NO:31:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:31:

Ile Glu Ala Asp Ala
1               5

(2) INFORMATION FOR SEQ ID NO:32:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:32:

Gly Tyr Val Ser Phe Arg His Val Glu Glu Gly Ser Trp Tyr Ile
1               5                   10                  15

(2) INFORMATION FOR SEQ ID NO:33:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:33:

Gly Val Arg Asn Gly Thr
1               5

(2) INFORMATION FOR SEQ ID NO:34:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:34:

Leu Ser His Gly Glu Glu
1               5

(2) INFORMATION FOR SEQ ID NO:35:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:35:
```

```
Phe Ile Gln Ala Cys Arg Gly Thr Glu
1               5

(2) INFORMATION FOR SEQ ID NO:36:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:36:

Ile Gln Ala Asp Ser
1               5

(2) INFORMATION FOR SEQ ID NO:37:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:37:

Gly Tyr Tyr Ser Trp Arg Ser Pro Gly Arg Gly Ser Trp Phe Val
1               5                   10                  15

(2) INFORMATION FOR SEQ ID NO:38:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:38:

Pro Glu Arg Arg Gly Thr
1               5

(2) INFORMATION FOR SEQ ID NO:39:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:39:

Leu Ser His Gly Glu Gly
1               5

(2) INFORMATION FOR SEQ ID NO:40:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:40:

Ile Ile Gln Ala Cys Arg Gly Asn Gln
1               5
```

(2) INFORMATION FOR SEQ ID NO:41:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:41:

```
Asp Val Val Asp Asn
1               5
```

(2) INFORMATION FOR SEQ ID NO:42:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:42:

```
Thr Glu Val Asp Ala
1               5
```

(2) INFORMATION FOR SEQ ID NO:43:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:43:

```
Gly Tyr Tyr Ser His Arg Glu Thr Val Asn Gly Ser Trp Tyr Ile
1               5                   10                  15
```

(2) INFORMATION FOR SEQ ID NO:44:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:44:

```
Thr Ser Arg Ser Gly Thr
1               5
```

(2) INFORMATION FOR SEQ ID NO:45:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:45:

```
Leu Ser His Gly Glu Glu
1               5
```

(2) INFORMATION FOR SEQ ID NO:46:

(i) SEQUENCE CHARACTERISTICS:
        (A) LENGTH: 9 amino acids

```
            (B) TYPE: amino acid
            (D) TOPOLOGY: linear (ii) MOLECULE TYPE: peptide (xi) SEQUENCE DESCRIPTION: SEQ ID NO:46:

Ile Ile Gln Ala Cys Arg Gly Thr Glu
1               5

(2) INFORMATION FOR SEQ ID NO:47:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:47:

Ile Glu Thr Asp Ser
1               5

(2) INFORMATION FOR SEQ ID NO:48:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:48:

Gly Tyr Tyr Ser Trp Arg Asn Ser Lys Asp Gly Ser Trp Phe Ile
1               5                  10                  15

(2) INFORMATION FOR SEQ ID NO:49:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:49:

Pro Thr Arg Asn Gly Thr
1               5

(2) INFORMATION FOR SEQ ID NO:50:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:50:

Leu Ser His Gly Glu Glu
1               5

(2) INFORMATION FOR SEQ ID NO:51:

(i) SEQUENCE CHARACTERISTICS:
        (A) LENGTH: 9 amino acids
        (B) TYPE: amino acid
        (D) TOPOLOGY: linear (ii) MOLECULE TYPE: peptide
```

(xi) SEQUENCE DESCRIPTION: SEQ ID NO:51:

Phe Val Gln Ala Cys Arg Gly Glu Arg
1               5

(2) INFORMATION FOR SEQ ID NO:52:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:52:

Asp Ser Val Asp Gly
1               5

(2) INFORMATION FOR SEQ ID NO:53:

(i) SEQUENCE CHARACTERISTICS:
        (A) LENGTH: 15 amino acids
        (B) TYPE: amino acid
        (D) TOPOLOGY: linear (ii) MOLECULE TYPE: cDNA (xi) SEQUENCE DESCRIPTION: SEQ ID NO:53:

Gln Tyr Val Ser Trp Arg Asn Ser Ala Arg Gly Ser Trp Phe Ile
1               5                  10                  15

(2) INFORMATION FOR SEQ ID NO:54:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:54:

Pro Arg Arg Thr Gly Ala
1               5

(2) INFORMATION FOR SEQ ID NO:55:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:55:

Met Ser His Gly Ile Arg
1               5

(2) INFORMATION FOR SEQ ID NO:56:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:56:

Ile Ile Gln Ala Cys Arg Gly Asp Ser

```
1               5
```

(2) INFORMATION FOR SEQ ID NO:57:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:57:

```
Trp Phe Lys Asp Ser
1               5
```

(2) INFORMATION FOR SEQ ID NO:58:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:58:

```
Phe Glu Asp Asp Ala
1               5
```

(2) INFORMATION FOR SEQ ID NO:59:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:59:

```
Asp Asn Val Ser Trp Arg His Pro Thr Met Gly Ser Val Phe Ile
1               5                   10                  15
```

(2) INFORMATION FOR SEQ ID NO:60:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:60:

```
Pro Pro Arg Asn Gly Ala
1               5
```

(2) INFORMATION FOR SEQ ID NO:61:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:61:

```
Met Ser His Gly Ile Leu
1               5
```

(2) INFORMATION FOR SEQ ID NO:62:

(i) SEQUENCE CHARACTERISTICS:
              (A) LENGTH: 9 amino acids
              (B) TYPE: amino acid
              (D) TOPOLOGY: linear (ii) MOLECULE TYPE: peptide (xi) SEQUENCE DESCRIPTION: SEQ ID NO:62:

Ile Val Gln Ala Cys Arg Gly Ala Asn
1               5

(2) INFORMATION FOR SEQ ID NO:63:

(i) SEQUENCE CHARACTERISTICS:
              (A) LENGTH: 5 amino acids
              (B) TYPE: amino acid
              (D) TOPOLOGY: linear (ii) MOLECULE TYPE: peptide (xi) SEQUENCE DESCRIPTION: SEQ ID NO:63:

Trp Val Lys Asp Ser
1               5

(2) INFORMATION FOR SEQ ID NO:64:

(i) SEQUENCE CHARACTERISTICS:
              (A) LENGTH: 5 amino acids
              (B) TYPE: amino acid
              (D) TOPOLOGY: linear (ii) MOLECULE TYPE: peptide (xi) SEQUENCE DESCRIPTION: SEQ ID NO:64:

Leu Glu Glu Asp Ala
1               5

(2) INFORMATION FOR SEQ ID NO:65:

(i) SEQUENCE CHARACTERISTICS:
              (A) LENGTH: 15 amino acids
              (B) TYPE: amino acid
              (D) TOPOLOGY: linear (ii) MOLECULE TYPE: peptide (xi) SEQUENCE DESCRIPTION: SEQ ID NO:65:

His Asn Val Ser Trp Arg Asp Ser Thr Met Gly Ser Ile Phe Ile
1               5                  10                  15

(2) INFORMATION FOR SEQ ID NO:66:

(i) SEQUENCE CHARACTERISTICS:
              (A) LENGTH: 6 amino acids
              (B) TYPE: amino acid
              (D) TOPOLOGY: linear (ii) MOLECULE TYPE: peptide (xi) SEQUENCE DESCRIPTION: SEQ ID NO:66:

Pro Ala Arg Asn Gly Ala
1               5

(2) INFORMATION FOR SEQ ID NO:67:

(i) SEQUENCE CHARACTERISTICS:
              (A) LENGTH: 6 amino acids
              (B) TYPE: amino acid (D) TOPOLOGY: linear (ii) MOLECULE TYPE: peptide (xi) SEQUENCE DESCRIPTION: SEQ ID NO:67:

Met Ser His Gly Ile Leu
1               5

(2) INFORMATION FOR SEQ ID NO:68:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:68:

Ile Val Gln Ala Cys Arg Gly Glu Lys
1               5

(2) INFORMATION FOR SEQ ID NO:69:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:69:

Trp Val Arg Asp Ser
1               5

(2) INFORMATION FOR SEQ ID NO:70:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:70:

Leu Glu Ala Asp Ser
1               5

(2) INFORMATION FOR SEQ ID NO:71:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:71:

His Asn Val Ser Trp Arg Asp Arg Thr Arg Gly Ser Ile Phe Ile
1               5                   10                  15

(2) INFORMATION FOR SEQ ID NO:72:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:72:

Glu Phe Arg Ser Gly Gly
1               5

(2) INFORMATION FOR SEQ ID NO:73:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:73:

Leu Ser His Gly Val Glu
1               5

(2) INFORMATION FOR SEQ ID NO:74:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:74:

Phe Ile Gln Ala Cys Arg Gly Asp Glu
1               5

(2) INFORMATION FOR SEQ ID NO:75:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:75:

Asp Gln Gln Asp Gly
1               5

(2) INFORMATION FOR SEQ ID NO:76:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:76:

Glu Glu Ser Asp Ala
1               5

(2) INFORMATION FOR SEQ ID NO:77:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:77:

Gly Thr Ala Ala Met Arg Asn Thr Lys Arg Gly Ser Trp Tyr Ile
1               5                   10                  15

(2) INFORMATION FOR SEQ ID NO:78:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:78:

Gln Ala Cys Gly Gly
1               5

(2) INFORMATION FOR SEQ ID NO:79:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:79:

Gln Ala Cys Arg Gly
1               5

(2) INFORMATION FOR SEQ ID NO:80:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:80:

Gln Ala Cys Gln Gly
1               5

(2) INFORMATION FOR SEQ ID NO:81:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 4
        (D) OTHER INFORMATION: /note= "Amino Acid is bonded to an
            aldehyde at the C-terminal."

(xi) SEQUENCE DESCRIPTION: SEQ ID NO:81:

Asp Glu Val Asp
1

(2) INFORMATION FOR SEQ ID NO:82:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Peptide (B) LOCATION: 4
            (D) OTHER INFORMATION: /note= "Amino acid is bonded to an
                aminomethylcoumarin at the C-terminal."

(xi) SEQUENCE DESCRIPTION: SEQ ID NO:82:

Asp Glu Val Asp
1

(2) INFORMATION FOR SEQ ID NO:83:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 4
        (D) OTHER INFORMATION: /note= "Amino acid is bonded to
            aminomethylcoumarin at the C-terminal."

(xi) SEQUENCE DESCRIPTION: SEQ ID NO:83:

Tyr Val Ala Asp
1

(2) INFORMATION FOR SEQ ID NO:84:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:84:

Pro Glu Pro Asp Ala
1               5

(2) INFORMATION FOR SEQ ID NO:85:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:85:

Asp Gln Leu Asp Ala
1               5

(2) INFORMATION FOR SEQ ID NO:86:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:86:

Asp Glu Val Asp Gly
1               5

(2) INFORMATION FOR SEQ ID NO:87:

(i) SEQUENCE CHARACTERISTICS:

```
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:87:

Asp Val Val Asp Asn
1               5
```